(12) United States Patent
Egoyants et al.

(10) Patent No.: US 9,357,803 B2
(45) Date of Patent: Jun. 7, 2016

(54) HEAT INSULATED APPARATUS FOR HEATING SMOKABLE MATERIAL

(75) Inventors: Petr Alexandrovich Egoyants, St. Petersburg (RU); Dmitry Mikhailovich Volobuev, St. Petersburg (RU); Pavel Nikolaevich Fimin, St. Petersburg (RU); Fozia Saleem, London (GB); Thomas Woodman, London (GB)

(73) Assignee: British American Tobacco (Investments) Limited, London (GB)

( * ) Notice: Subject to any disclaimer, the term of this patent is extended or adjusted under 35 U.S.C. 154(b) by 0 days.

(21) Appl. No.: 14/127,879

(22) PCT Filed: Aug. 24, 2012

(86) PCT No.: PCT/EP2012/066523
§ 371 (c)(1),
(2), (4) Date: May 9, 2014

(87) PCT Pub. No.: WO2013/034458
PCT Pub. Date: Mar. 14, 2013

(65) Prior Publication Data
US 2014/0270726 A1    Sep. 18, 2014

(30) Foreign Application Priority Data

Sep. 6, 2011   (RU) ................................ 2011136872
Apr. 23, 2012  (GB) .................................. 1207054.6

(51) Int. Cl.
*A01M 13/00*   (2006.01)
*A24F 47/00*   (2006.01)
*F16L 59/065*  (2006.01)

(52) U.S. Cl.
CPC ............ *A24F 47/008* (2013.01); *A24F 47/004* (2013.01); *F16L 59/065* (2013.01)

(58) Field of Classification Search
None
See application file for complete search history.

(56) References Cited

U.S. PATENT DOCUMENTS

| | | | |
|---|---|---|---|
| 1,886,391 A | | 11/1932 | Gauvin |
| 2,104,266 A | * | 1/1938 | McCormick ............... 131/198.1 |
| 3,804,100 A | | 4/1974 | Fariello |
| 3,805,806 A | | 4/1974 | Grihalva |
| 3,889,690 A | | 6/1975 | Guarnieri |
| 4,171,000 A | | 10/1979 | Uhle |
| 4,303,083 A | * | 12/1981 | Burruss, Jr. ................... 131/271 |
| 4,474,191 A | * | 10/1984 | Steiner ....................... 131/198.2 |
| 4,588,976 A | | 5/1986 | Jaselli |
| 4,638,820 A | | 1/1987 | Roberts et al. |

(Continued)

FOREIGN PATENT DOCUMENTS

| CN | 86102917 | 11/1987 |
|---|---|---|
| CN | 86102917 A | 11/1987 |

(Continued)

OTHER PUBLICATIONS

International Search Report and Written Opinion, mailed Jan. 9, 2013, for PCT/EP2012/066523, filed Aug. 24, 2012.

(Continued)

*Primary Examiner* — Thor Campbell
(74) *Attorney, Agent, or Firm* — Patterson Thuente Pedersen, P.A.

(57) ABSTRACT

An apparatus configured to heat smokable material to volatilize at least one component of the smokable material, wherein the apparatus comprises a region insulation having a core region which is evacuated to a lower pressure than an exterior of the insulation.

11 Claims, 11 Drawing Sheets

(56) References Cited

U.S. PATENT DOCUMENTS

| | | | | |
|---|---|---|---|---|
| 4,735,217 A | | 4/1988 | Gerth et al. | |
| 4,756,318 A | * | 7/1988 | Clearman et al. | 131/359 |
| 4,765,347 A | * | 8/1988 | Sensabaugh et al. | 131/273 |
| 4,907,606 A | * | 3/1990 | Lilja et al. | 131/273 |
| 4,922,901 A | | 5/1990 | Brooks et al. | |
| 4,945,929 A | | 8/1990 | Egilmex | |
| 4,945,931 A | | 8/1990 | Gori | |
| 4,947,874 A | | 8/1990 | Brooks et al. | |
| 4,947,875 A | * | 8/1990 | Brooks et al. | 131/330 |
| 5,040,551 A | * | 8/1991 | Schlatter et al. | 131/359 |
| 5,060,671 A | | 10/1991 | Counts et al. | |
| 5,095,921 A | | 3/1992 | Losee et al. | |
| 5,179,966 A | | 1/1993 | Losee et al. | |
| 5,190,060 A | | 3/1993 | Gerding et al. | |
| 5,224,498 A | | 7/1993 | Deevi et al. | |
| 5,249,586 A | * | 10/1993 | Morgan et al. | 131/194 |
| 5,269,327 A | | 12/1993 | Counts et al. | |
| 5,285,798 A | * | 2/1994 | Banerjee et al. | 131/194 |
| 5,303,720 A | * | 4/1994 | Banerjee et al. | 131/194 |
| 5,322,075 A | | 6/1994 | Deevi et al. | |
| 5,327,915 A | | 7/1994 | Porenski et al. | |
| 5,331,979 A | * | 7/1994 | Henley | 131/273 |
| 5,345,951 A | * | 9/1994 | Serrano et al. | 131/194 |
| 5,369,723 A | * | 11/1994 | Counts et al. | 392/386 |
| 5,388,594 A | | 2/1995 | Counts et al. | |
| 5,402,803 A | | 4/1995 | Takagi | |
| 5,408,574 A | | 4/1995 | Deevi et al. | |
| 5,573,140 A | | 11/1996 | Satomi et al. | |
| 5,613,504 A | * | 3/1997 | Collins et al. | 131/94 |
| 5,613,505 A | | 3/1997 | Campbell et al. | |
| 5,665,262 A | * | 9/1997 | Hajaligol et al. | 219/553 |
| 5,771,845 A | | 6/1998 | Pistien et al. | |
| 5,865,186 A | | 2/1999 | Volsey, II | |
| 6,089,857 A | | 7/2000 | Matsuura et al. | |
| 6,155,268 A | | 12/2000 | Takeuchi | |
| 7,374,063 B2 | * | 5/2008 | Reid | 220/592.27 |
| 7,624,739 B2 | * | 12/2009 | Snaidr et al. | 131/187 |
| 7,913,688 B2 | * | 3/2011 | Cross et al. | 128/203.26 |
| 8,061,361 B2 | * | 11/2011 | Maeder et al. | 131/270 |
| 8,079,371 B2 | * | 12/2011 | Robinson et al. | 131/200 |
| 8,678,013 B2 | * | 3/2014 | Crooks et al. | 131/273 |
| 8,807,140 B1 | * | 8/2014 | Scatterday | 131/273 |
| 8,833,364 B2 | | 9/2014 | Buchberger | |
| 2003/0049025 A1 | | 3/2003 | Neumann et al. | |
| 2004/0003820 A1 | | 1/2004 | Iannuzzi | |
| 2004/0096204 A1 | | 5/2004 | Gerhardinger | |
| 2005/0063686 A1 | | 3/2005 | Whittle et al. | |
| 2005/0211711 A1 | | 9/2005 | Reid | |
| 2005/0268911 A1 | | 12/2005 | Cross et al. | |
| 2007/0074734 A1 | | 4/2007 | Braunshteyn et al. | |
| 2007/0155255 A1 | | 7/2007 | Galauner et al. | |
| 2007/0204858 A1 | | 9/2007 | Abelbeck | |
| 2007/0204868 A1 | | 9/2007 | Bollinger | |
| 2007/0283972 A1 | | 12/2007 | Monsees | |
| 2008/0092912 A1 | | 4/2008 | Robinson et al. | |
| 2008/0216828 A1 | | 9/2008 | Wensley et al. | |
| 2008/0233318 A1 | * | 9/2008 | Coyle | 428/34.1 |
| 2008/0302374 A1 | | 12/2008 | Wengert et al. | |
| 2009/0032034 A1 | | 2/2009 | Steinberg | |
| 2009/0056728 A1 | | 3/2009 | Baker | |
| 2009/0126745 A1 | | 5/2009 | Hon | |
| 2009/0151717 A1 | | 6/2009 | Bowen et al. | |
| 2009/0272379 A1 | | 11/2009 | Thorens et al. | |
| 2010/0126516 A1 | | 5/2010 | Yomtov et al. | |
| 2010/0242975 A1 | | 9/2010 | Hearn | |
| 2011/0126848 A1 | | 6/2011 | Zuber et al. | |
| 2011/0155153 A1 | | 6/2011 | Thorens et al. | |
| 2012/0006342 A1 | | 1/2012 | Rose et al. | |
| 2012/0255546 A1 | | 10/2012 | Goetz et al. | |
| 2013/0081623 A1 | | 4/2013 | Buchberger | |
| 2014/0182608 A1 | | 7/2014 | Egoyants et al. | |
| 2014/0182843 A1 | * | 7/2014 | Vinegar | 166/250.01 |
| 2014/0202476 A1 | | 7/2014 | Egoyants et al. | |
| 2014/0216485 A1 | | 8/2014 | Egoyants et al. | |
| 2014/0283825 A1 | | 9/2014 | Buchberger | |
| 2014/0299125 A1 | | 10/2014 | Buchberger | |
| 2014/0305449 A1 | | 10/2014 | Plojoux | |
| 2014/0326257 A1 | | 11/2014 | Jalloul et al. | |
| 2014/0338680 A1 | | 11/2014 | Abramov et al. | |
| 2014/0360515 A1 | | 12/2014 | Vasiliev et al. | |
| 2015/0040925 A1 | | 2/2015 | Saleem et al. | |
| 2015/0223520 A1 | | 8/2015 | Phillips et al. | |

FOREIGN PATENT DOCUMENTS

| | | | |
|---|---|---|---|
| CN | 1040914 | | 4/1990 |
| CN | 1040914 | A | 4/1990 |
| CN | 1045691 | | 10/1990 |
| CN | 1045691 | A | 10/1990 |
| CN | 119661 | | 10/1998 |
| CN | 1196661 | A | 10/1998 |
| CN | 2598364 | | 1/2004 |
| CN | 101238047 | | 8/2008 |
| CN | 101238047 | A | 8/2008 |
| CN | 101267749 | | 9/2008 |
| CN | 101277622 | | 10/2008 |
| CN | 201185656 | | 1/2009 |
| CN | 201185656 | Y | 1/2009 |
| CN | 101557728 | | 10/2009 |
| CN | 201375023 | | 1/2010 |
| DE | 29713866 | | 10/1997 |
| EP | 0358002 | | 3/1990 |
| EP | 0358002 | A2 | 3/1990 |
| EP | 0358114 | | 3/1990 |
| EP | 0358114 | A2 | 3/1990 |
| EP | 0430559 | A2 | 6/1991 |
| EP | 0438862 | | 7/1991 |
| EP | 0488488 | | 6/1992 |
| EP | 0503767 | | 9/1992 |
| EP | 0603613 | | 6/1994 |
| EP | 2316286 | | 5/2001 |
| EP | 1618803 | | 1/2006 |
| EP | 1736065 | | 12/2006 |
| EP | 2022349 | | 2/2009 |
| EP | 2110033 | | 10/2009 |
| EP | 2327318 | | 6/2011 |
| EP | 2340730 | | 7/2011 |
| EP | 2394520 | | 12/2011 |
| GB | 426247 | | 3/1935 |
| JP | 62501050 | A | 4/1987 |
| JP | 63127399 | | 8/1988 |
| JP | 03192677 | | 8/1991 |
| JP | 03232481 | A | 10/1991 |
| JP | 6189861 | | 7/1994 |
| JP | 06315366 | | 11/1994 |
| JP | 08000942 | | 6/1996 |
| JP | 09107943 | | 4/1997 |
| JP | 1189551 | | 4/1999 |
| JP | 11125390 | | 5/1999 |
| JP | 11169157 | | 6/1999 |
| JP | 2005036897 | | 2/2005 |
| JP | 2005036897 | A | 2/2005 |
| JP | 2005106350 | | 4/2005 |
| JP | 2005106350 | A | 4/2005 |
| JP | 2006501871 | | 1/2006 |
| JP | 2008249003 | | 10/2008 |
| JP | 2008249003 | A | 10/2008 |
| JP | 2009537120 | | 10/2009 |
| JP | 2010506594 | | 3/2010 |
| JP | 2010178730 | | 8/2010 |
| JP | 2010213579 | | 9/2010 |
| JP | 2011509667 | | 3/2011 |
| JP | 2011509667 | A | 3/2011 |
| WO | 8602528 | A1 | 5/1986 |
| WO | WO0167819 | | 9/2001 |
| WO | WO03037412 | | 5/2003 |
| WO | WO03059413 | | 7/2003 |
| WO | WO03103387 | | 12/2003 |
| WO | 2007017482 | A1 | 2/2007 |
| WO | WO2007017482 | | 2/2007 |
| WO | WO2007131450 | | 11/2007 |
| WO | WO2008108889 | | 9/2008 |
| WO | WO2009001082 | | 12/2008 |
| WO | 2009092862 | A1 | 7/2009 |

(56) References Cited

FOREIGN PATENT DOCUMENTS

| WO | WO2009092862 | | 7/2009 |
|---|---|---|---|
| WO | WO2010073018 | | 7/2010 |
| WO | 2010107613 | A1 | 9/2010 |
| WO | WO2010107613 | | 9/2010 |
| WO | WO2010118644 | | 10/2010 |
| WO | 2011050964 | A1 | 5/2011 |
| WO | WO2011050964 | | 5/2011 |

OTHER PUBLICATIONS

International Preliminary Report on Patentability, mailed Nov. 4, 2013, for PCT/EP2012/066523, filed Aug. 24, 2012.
Office Action (with machine English translation), mailed Apr. 7, 2015, for JP 2014-519586, referencing JP 03-232481, US 2005/0211711, WO 2011/050964, JP 62-501050, JP 2008-249003, JP 2011-509667, JP 2005-36897, and JP 2005-106350.
Application and File History for U.S. Appl. No. 14/382,198, filed Aug. 29, 2014, inventors Saleem et al.
Application and File History for U.S. Appl. No. 14/127,144, filed Mar. 31, 2014, inventors Egoyants et al.
Application and File History for U.S. Appl. No. 14/127,138, filed Feb. 10, 2014, inventors Egoyants et al.
Application and File History for U.S. Appl. No. 14/127,133, filed Jul. 15, 2014, inventors Vasiliev et al.
Office Action and Search Report (with English Translation) mailed Apr. 27, 2015, for CN201280030681.5.
Office Action (with English Translation) mailed Apr. 7, 2015 for JP2014519586.
International Search Report and Written Opinion, mailed Jan. 9, 2013, for International Application No. PCT/EP2012/066523 filed Aug. 24, 2012.
International Preliminary Report on Patentability, mailed Nov. 4, 2013, for International Application No. PCT/EP2012/066523 filed Aug. 24, 2012.
Search Report dated Mar. 24, 2015, for Chinese Patent Application No. 201280029767.6 filed Aug. 24, 2012 (including English Translation).
International Search Report and Written Opinion, mailed Jan. 9, 2013 for International Application No. PCT/EP2012/066524, filed Aug. 24, 2012.
International Preliminary Report on Patentability, mailed Oct. 17, 2013 for International Application No. PCT/EP2012/066524, filed Aug. 24, 2012.
International Search Report and Written Opinion, mailed Dec. 10, 2012, for PCT/EP2012/066485, filed Aug. 24, 2012.
Written Opinion, mailed Oct. 15, 2013, for PCT/EP2012/066485, filed Aug. 24, 2012.
International Search Report and Written Opinion, mailed Jan. 9, 2013, for International Application No. PCT/EP2012/066484, filed Aug. 24, 2012.
International Search Report and Written Opinion mailed Feb. 11, 2014 for PCT/EP2013/057539 filed Apr. 11, 2013.
Warrier et al., "Effect of the Porous Structure of Graphite on Atomic Hydrogen Diffusion and Inventory". Nucl. Fusion 47(2007) 1656-1663, DOI: 10.1088/0029-5515/47/12/003.
Davies et al., (1983) Metallic Foams: Their Production, Properties and Applications. Journal of Materials Science, vol. 18 (7). p. 1899-1911.
Application and File History for U.S. Appl. No. 13/583,381, filed Dec. 17, 2012, inventor Buchberger.
International Search Report dated Jul. 18, 2011 issued in corresponding International Patent Application No. PCT/AT2011/000123.
Office Action and Search Report (with English translation), mailed Apr. 27, 2015, for CN 201280030681.5, referencing CN1040914A, CN86102917A, CN101238047A, CN1045691A, CN1196661A, CN201185656Y.
Chinese First Office Action for Chinese Patent Application No. 201380021387.2 dated Dec. 3, 2015. English translation provided.
Application and File History for U.S. Appl. No. 14/127,148 filed Mar. 12, 2014, inventors Egoyants et al.
Application and File History for U.S. Appl. No. 14/343,368 filed Jun. 24, 2014, inventors Abramov et al.
International Search Report and Written Opinion mailed Jan. 14, 2013 for PCT/EP2012/066486 filed Aug. 24, 2012.
International Preliminary Report on Patentability and response thereto mailed Oct. 22, 2013 for PCT/EP2012/066486 filed Aug. 24, 2012.
Office Action (with English translation) dated Mar. 31, 2015 for JP2014-519585, referencing JP2010-506594, JP03-232481, JP2010-213579, JP62-17980, JP2006-501871, JP4-78508 and JP62-501050.
First Office Action (dated Jun. 15, 2015) and Search Report (dated Jun. 2, 2015) for Chinese Patent Application No. 201280029784.X filed Aug. 24, 2012.
International Search Report and Written Opinion mailed Jan. 9, 2013 for PCT/EP2012/066525 filed Aug. 24, 2012.

* cited by examiner

HEAT INSULATED APPARATUS FOR HEATING SMOKABLE MATERIAL

CLAIM FOR PRIORITY

This application is a National Stage Entry of and claims priority under 35 U.S.C. §§365 and 371 to PCT application serial no. PCT/EP2012/066523, filed Aug. 24, 2012 and entitled "Heat Insulated Apparatus for Heating Smokable Material," which in turn claims priority to Russian Application Serial No. 2011 136 872, filed Sep. 6, 2011 and entitled "Heating Smokable Material," and to British Application Serial No. 1207054.6, filed 23 Apr. 2012 and entitled "Heating smokable material." The entire contents of the aforementioned applications are herein expressly incorporated by reference.

FIELD

The invention relates to heating smokable material.

BACKGROUND

Smoking articles such as cigarettes and cigars burn tobacco during use to create tobacco smoke. Attempts have been made to provide alternatives to these smoking articles by creating products which release compounds without creating tobacco smoke. Examples of such products are so-called heat-not-burn products which release compounds by heating, but not burning, tobacco.

SUMMARY

According to the invention, there is provided an apparatus configured to heat smokable material to volatilize at least one component of the smokable material, wherein the apparatus comprises a region of insulation having a core region which is evacuated to a lower pressure than an exterior of the insulation.

The insulation may be located between a smokable material heating chamber and an exterior of the apparatus to reduce heat loss from heated smokable material.

The insulation may be located co-axially around the heating chamber.

The smokable material heating chamber may comprise a substantially tubular heating chamber and the insulation may be located around a longitudinal surface of the tubular heating chamber.

The insulation may comprise a substantially tubular body of insulation located around the heating chamber.

The smokable material heating chamber may be located between the insulation and a heater.

A heater may be located between the smokable material heating chamber and the insulation.

The insulation may be located externally of the heater.

The heater may be located co-axially around the heating chamber and the insulation may be located co-axially around the heater.

The insulation may comprise an infra-red radiation-reflective material to reduce the propagation of the infra-red radiation through the insulation.

The insulation may comprise an exterior wall which encloses the core region.

An internal surface of the wall may comprise an infra-red radiation-reflective coating to reflect infra-red radiation within the core region.

The wall may comprise a layer of stainless steel having a thickness of at least approximately 100 microns.

Wall sections either side of the core region may be connected by a joining wall section which follows an indirect path between the sections either side of the core region.

A pressure in the core region may be between approximately 0.1 and approximately 0.001 mbar.

A heat transfer coefficient of the insulation may be between approximately 1.10 W/(m$^2$K) and approximately 1.40 W/(m$^2$K) when a temperature of the insulation is in a range of from 100 degrees Celsius to 250 degrees Celsius, such as in a range from 150 degrees Celsius to 250 degrees Celsius.

The core region may comprise a porous material.

Wall sections either side of the core region may converge to a sealed gas outlet.

Said wall sections may converge in an end region of the insulation.

A thickness of the insulation may be less than approximately 1 mm.

A thickness of the insulation may be less than approximately 0.1 mm.

A thickness of the insulation may be between approximately 1 mm and 0.001 mm.

The apparatus may be configured to heat the smokable material using an electrically-powered heater.

The apparatus may be configured to heat the smokable material without combusting the smokable material.

According to an aspect of the invention, there is provided an apparatus configured to heat smokable material to volatilize at least one component of the smokable material, comprising an infra-red heater.

The infra-red heater may comprise a halogen infra-red heater.

For exemplary purposes only, embodiments of the invention are described below with reference to the accompanying figures in which:

DETAILED DESCRIPTION

Figure 1:
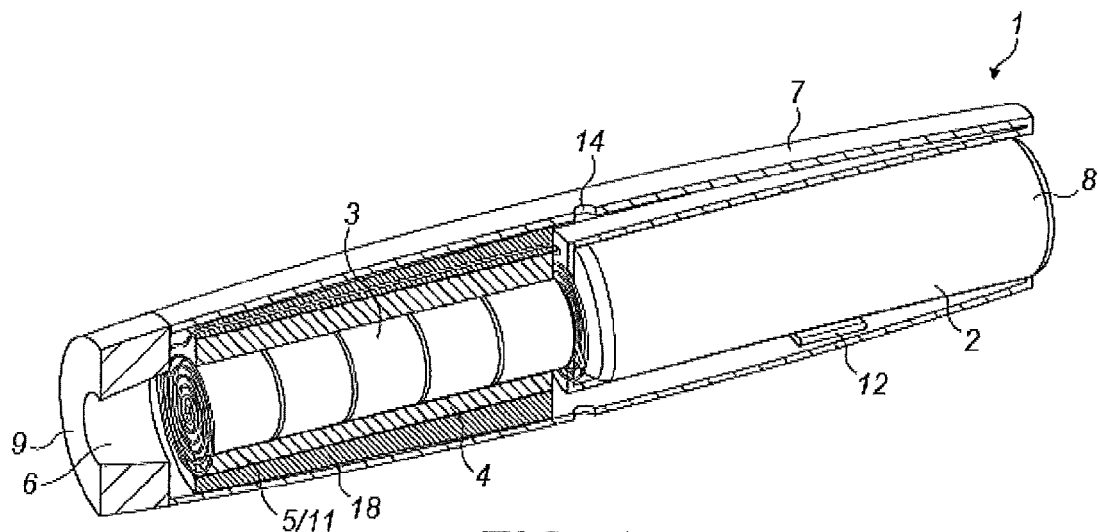
FIG. 1 is a perspective, partially cut-away illustration of an apparatus configured to heat smokable material to release aromatic compounds and/or nicotine from the smokable material.

As used herein, the term 'smokable material' includes any material that provides volatilized components upon heating and includes any tobacco-containing material and may, for example, include one or more of tobacco, tobacco derivatives, expanded tobacco, reconstituted tobacco or tobacco substitutes.

An apparatus 1 for heating smokable material comprises an energy source 2, a heater 3 and a heating chamber 4. The energy source 2 may comprise a battery such as a Li-ion battery, Ni battery, Alkaline battery and/or the like, and is electrically coupled to the heater 3 to supply electrical energy to the heater 3 when required. The heating chamber 4 is configured to receive smokable material 5 so that the smokable material 5 can be heated in the heating chamber 4. For example, the heating chamber 4 may be located adjacent to the heater 3 so that thermal energy from the heater 3 heats the smokable material 5 therein to volatilize aromatic compounds and nicotine in the smokable material 5 without burning the smokable material 5. A mouthpiece 6 is provided through which a user of the apparatus 1 can inhale the volatilized compounds during use of the apparatus 1. The smokable material 5 may comprise a tobacco blend.

As shown in FIG. 1, the heater 3 may comprise a substantially cylindrical, elongate heater 3 and the heating chamber 4 is located around a circumferential, longitudinal surface of the heater 3. The heating chamber 4 and smokable material 5 therefore comprise co-axial layers around the heater 3. However, as will be evident from the discussion below, other shapes and configurations of the heater 3 and heating chamber 4 can alternatively be used.

A housing 7 may contain components of the apparatus 1 such as the energy source 2 and heater 3. As shown in FIG. 1, the housing 7 may comprise an approximately cylindrical tube with the energy source 2 located towards its first end 8 and the heater 3 and heating chamber 4 located towards its opposite, second end 9. The energy source 2 and heater 3 extend along the longitudinal axis of the housing 7. For example, as shown in FIG. 1, the energy source 2 and heater 3 can be aligned along the central longitudinal axis of the housing 7 in an end-to-end arrangement so that an end face of the energy source 2 faces an end face of the heater 3. The length of the housing 7 may be approximately 130 mm, the length of energy source may be approximately 59 mm, and the length of the heater 3 and heating region 4 may be approximately 50 mm. The diameter of the housing 7 may be between approximately 15 mm and approximately 18 mm. For example, the diameter of the housing's first end 8 may be 18 mm whilst the diameter of the mouthpiece 6 at the housing's second end 9 may be 15 mm. The diameter of the heater 3 may be between approximately 2.0 mm and approximately 6.0 mm. The diameter of the heater 3 may, for example, be between approximately 4.0 mm and approximately 4.5 mm or between approximately 2.0 mm and approximately 3.0 mm. Heater diameters outside these ranges may alternatively be used. The depth of the heating chamber 4 may be approximately 5 mm and the heating chamber 4 may have an exterior diameter of approximately 10 mm at its outwardly-facing surface. The diameter of the energy source 2 may be between approximately 14.0 mm and approximately 15.0 mm, such as 14.6 mm.

Heat insulation may be provided between the energy source 2 and the heater 3 to prevent direct transfer of heat from one to the other. The mouthpiece 6 can be located at the second end 9 of the housing 7, adjacent the heating chamber 4 and smokable material 5. The housing 7 is suitable for being gripped by a user during use of the apparatus 1 so that the user can inhale volatilized smokable material compounds from the mouthpiece 6 of the apparatus 1.

Figure 2:
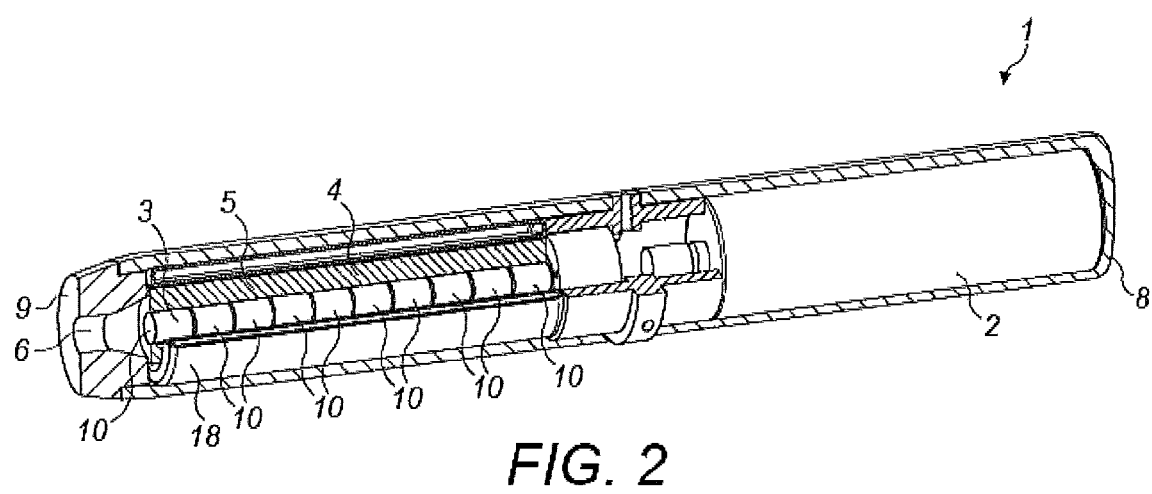
FIG. 2 is a perspective, partially cut-away illustration of an apparatus configured to heat smokable material, in which the smokable material is provided around an elongate ceramic heater divided into radial heating sections.
Figure 3:
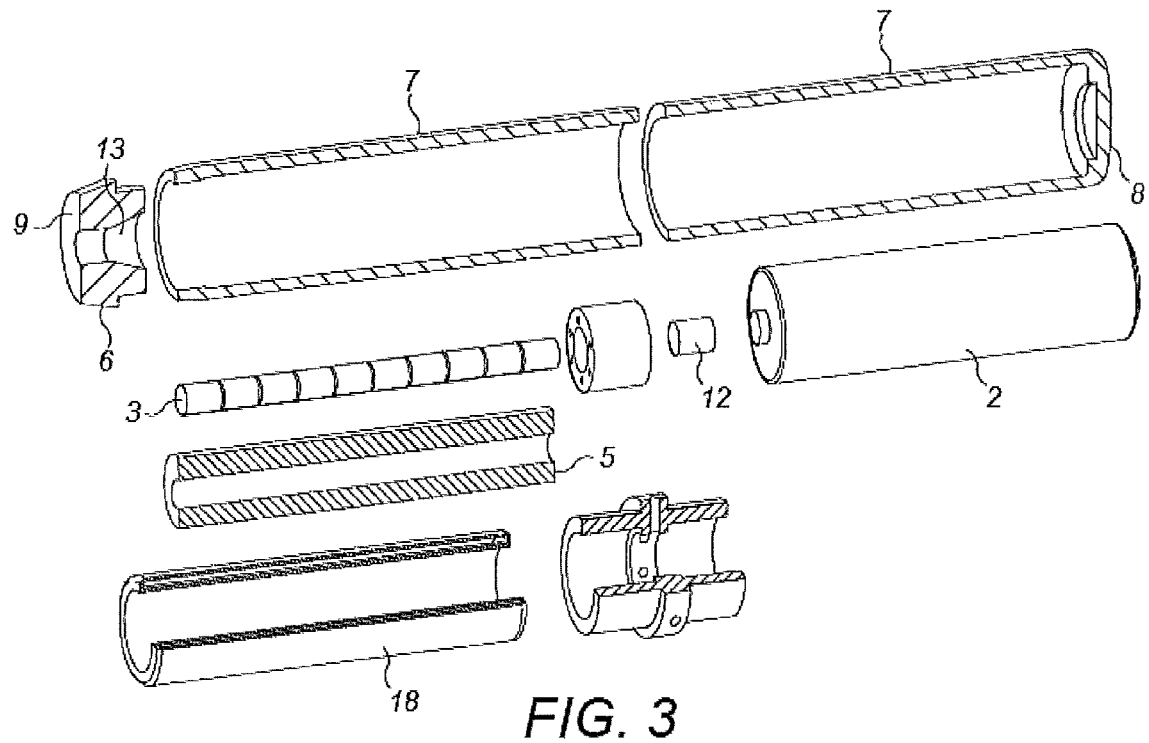
FIG. 3 is an exploded, partially cut-away view of an apparatus configured to heat smokable material, in which the smokable material is provided around an elongate ceramic heater divided into radial heating sections.
Figure 4:
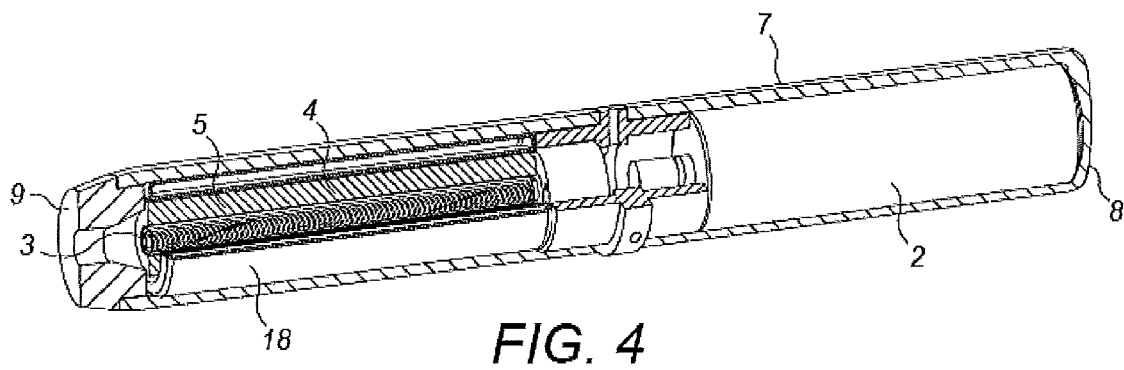
FIG. 4 is a perspective, partially cut-away illustration of an apparatus configured to heat smokable material, in which the smokable material is provided around an elongate infra-red heater.
Figure 5:
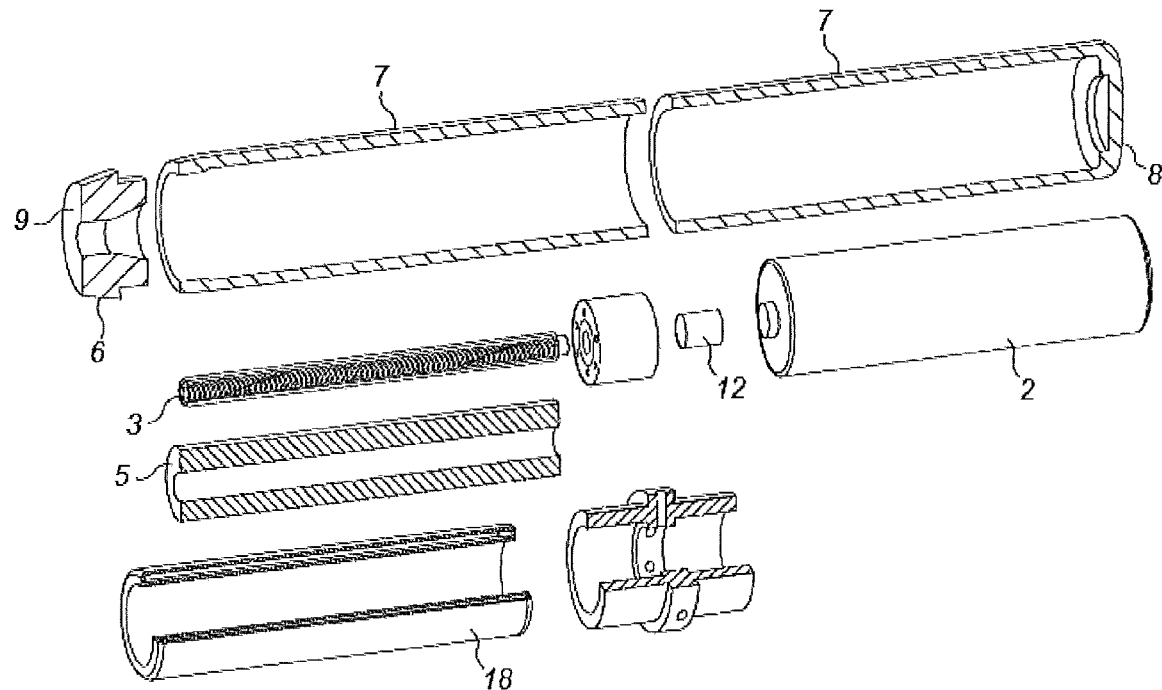
FIG. 5 is an exploded, partially cut-away illustration of an apparatus configured to heat smokable material, in which the smokable material is provided around an elongate infra-red heater.

Referring to FIGS. 2 and 3, the heater 3 may comprise a ceramics heater 3. The ceramics heater 3 may, for example, comprise base ceramics of alumina and/or silicon nitride which are laminated and sintered. Alternatively, referring to FIGS. 4 and 5, the heater 3 may comprise an infra-red (IR) heater 3 such as a halogen-IR lamp 3. The IR heater 3 may have a low mass and therefore its use can help to reduce the overall mass of the apparatus 1. For example, the mass of the IR heater may be 20% to 30% less than the mass of a ceramics heater 3 having an equivalent heating power output. The IR heater 3 also has low thermal inertia and therefore is able to heat the smokable material 5 very rapidly in response to an activation stimulus. The IR heater 3 may be configured to emit IR electromagnetic radiation of between approximately 700 nm and 4.5 μm in wavelength.

As indicated above and shown in FIG. 1, the heater 3 may be located in a central region of the housing 7 and the heating chamber 4 and smokable material 5 may be located around the longitudinal surface of the heater 3. In this arrangement, thermal energy emitted by the heater 3 travels in a radial direction outwards from the longitudinal surface of the heater 3 into the heating chamber 4 and the smokable material 5.

The heater 3 may optionally comprise a plurality of individual heating regions 10. The heating regions 10 may be operable independently of one another so that different regions 10 can be activated at different times to heat the smokable material 5. The heating regions 10 may be arranged in the heater 3 in any geometric arrangement. However, in the examples shown in the figures, the heating regions 10 are geometrically arranged in the heater 3 so that different ones of the heating regions 10 are arranged to predominately and independently heat different regions of the smokable material 5.

For example, referring to FIG. 2, the heater 3 may comprise a plurality of axially aligned heating regions 10. The regions 10 may each comprise an individual element of the heater 3. The heating regions 10 may, for example, all be aligned with each other along a longitudinal axis of the heater 3, thus providing a plurality of independent heating zones along the length of the heater 3. Each heating region 10 may comprise a heating cylinder 10 having a finite length which is significantly less than the length of the heater 3 as a whole. The arrangement and features of the cylinders 10 are discussed below in terms of heating disks, where each disk has a depth which is equivalent to cylinder length. The heating disks 10 are arranged with their radial surfaces facing one another along the length of the heater 3. The radial surfaces of each disk 10 may touch the radial surfaces of its neighbouring disks 10. Alternatively, a heat insulating or heat reflecting layer may be present between the radial surfaces of the disks 10 so that thermal energy emitted from each one of the disks 10 does not substantially heat the neighbouring disks 10 and instead travels predominately outwards from the circumferential surface of the disk 10 into the heating chamber 4 and smokable material 5. Each disk 10 may have substantially the same dimensions as the other disks 10.

In this way, when a particular one of the heating regions 10 is activated, it supplies thermal energy to the smokable material 5 located radially around the heating region 10 without substantially heating the remainder of the smokable material 5. For example, referring to FIG. 2, the heated region of smokable material 5 may comprise a ring of smokable material 5 located around the heating disk 10 which has been activated. The smokable material 5 can therefore be heated in independent sections, for example rings, where each section corresponds to smokable material 5 located directly around a particular one of the heating regions 10 and has a mass and volume which is significantly less than the body of smokable material 5 as a whole.

Figure 6:
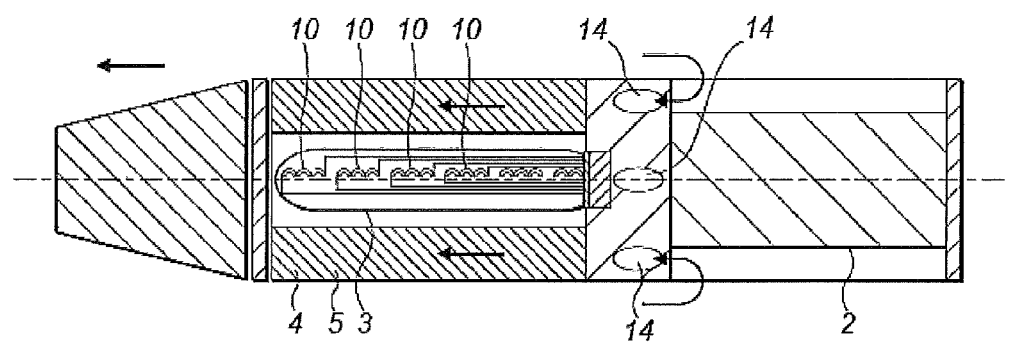
FIG. 6 is a schematic illustration of part of an apparatus configured to heat smokable material, in which the smokable material is provided around a plurality of longitudinal, elongate heating sections spaced around a central longitudinal axis.

Additionally or alternatively, referring to FIG. 6, the heater 3 may comprise a plurality of elongate, longitudinally extending heating regions 10 positioned at different locations around the central longitudinal axis of the heater 3. Although shown as being of different lengths in FIG. 6, the longitudinally extending heating regions 10 may be of substantially the same length so that each extends along substantially the whole length of the heater 3. Each heating region 10 may comprise, for example, an individual IR heating element 10 such as an IR heating filament 10. Optionally, a body of heat insulation or heat reflective material may be provided along the central longitudinal axis of the heater 3 so that thermal energy emitted by each heating region 10 travels predominately outwards from the heater 3 into the heating chamber 4 and thus heats the smokable material 5. The distance between the central longitudinal axis of the heater 3 and each of the heating regions 10 may be substantially equal. The heating regions 10 may optionally be contained in a substantially infra-red and/or heat transparent tube, or other housing, which forms a longitudinal surface of the heater 3. The heating regions 10 may be fixed in position relative to the other heating regions 10 inside the tube.

In this way, when a particular one of the heating regions 10 is activated, it supplies thermal energy to the smokable material 5 located adjacent to the heating region 10 without substantially heating the remainder of the smokable material 5. The heated section of smokable material 5 may comprise a longitudinal section of smokable material 5 which lies parallel and directly adjacent to the longitudinal heating region 10. Therefore, as with the previous example, the smokable material 5 can be heated in independent sections.

As will be described further below, the heating regions 10 can each be individually and selectively activated.

The smokable material 5 may be comprised in a cartridge 11 which can be inserted into the heating chamber 4. For example, as shown in FIG. 1, the cartridge 11 can comprise a smokable material tube 11 which can be inserted around the heater 3 so that the internal surface of the smokable material tube 11 faces the longitudinal surface of the heater 3. The smokable material tube 11 may be hollow. The diameter of the hollow centre of the tube 11 may be substantially equal to, or slightly larger than, the diameter of the heater 3 so that the tube 11 is a close fit around the heater 3. The length of the cartridge 11 may be approximately equal to the length of the heater 3 so that the heater 3 can heat the cartridge 11 along its whole length.

Figure 9:
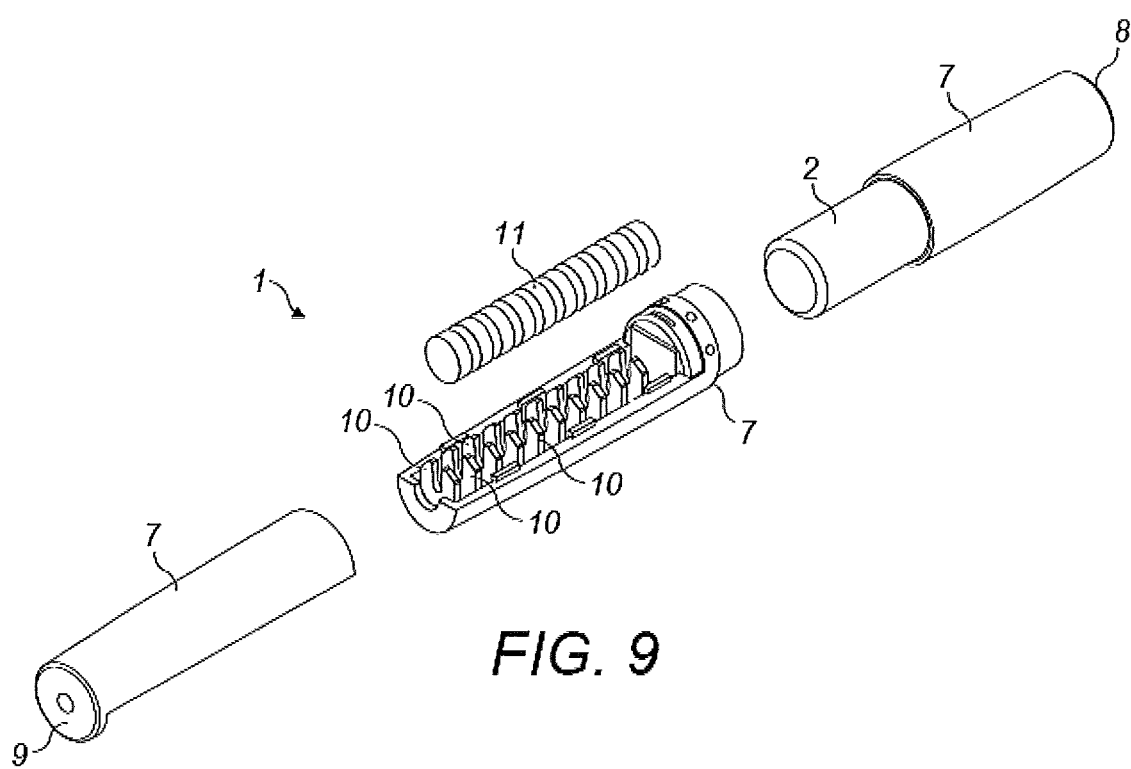
FIG. 9 is an exploded view of part of an apparatus configured to heat smokable material, in which the regions of smokable material are provided between pairs of upstanding heating plates.

The housing 7 of the apparatus 1 may comprise an opening through which the cartridge 11 can be inserted into the heating chamber 4. The opening may, for example, comprise a ring-shaped opening located at the housing's second end 9 so that the cartridge 11 can be slid into the opening and pushed directly into the heating chamber 4. The opening is preferably closed during use of the apparatus 1 to heat the smokable material 5. Alternatively, a section of the housing 7 at the second end 9 is removable from the apparatus 1 so that the smokable material 5 can be inserted into the heating chamber 4. An example of this is shown in FIG. 9. The apparatus 1 may optionally be equipped with a user-operable smokable material ejection unit, such as an internal mechanism configured to slide used smokable material 5 off and/or away from the heater 3. The used smokable material 5 may, for example, be pushed back through the opening in the housing 7. A new cartridge 11 can then be inserted as required.

In an alternative configuration of heater 3, the heater 3 comprises a spirally shaped heater 3. The spirally shaped heater 3 may be configured to screw into the smokable material cartridge 11 and may comprise adjacent, axially-aligned heating regions 10 so as to operate in substantially the same manner as described for the linear, elongate heater 3 described above.

Figure 21:
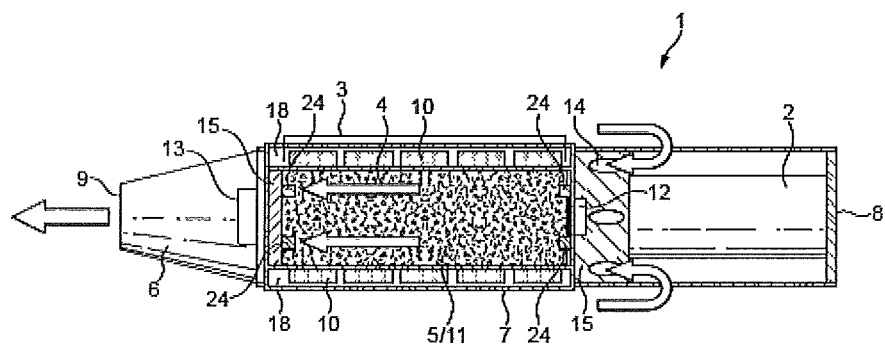
FIG. 21 is a schematic, cross sectional illustration of an apparatus configured to heat smokable material, in which a heater is located externally of a heating chamber and internally of thermal insulation.

In an alternative configuration of heater 3 and heating chamber 4, the heater 3 comprises a substantially elongate tube, which may be cylindrical, and the heating chamber 4 is located inside the tube 3 rather than around the heater's outside. The heater 3 may comprise a plurality of axially-aligned heating sections, which may each comprise a heating ring configured to heat smokable material 5 located radially inwardly from the ring. In this way, the heater 3 is configured to independently heat separate sections of smokable material 5 in the heating chamber 4 in a manner similar to the heater 3 described above in relation to FIG. 2. The heat is applied radially inwardly to the smokable material 5, rather than radially outwardly as previously described. An example is shown in FIG. 21.

Figure 7:
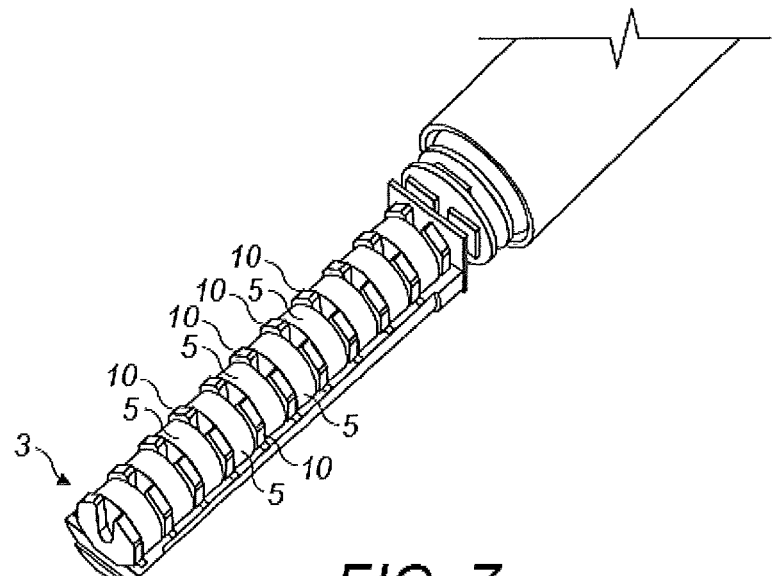
FIG. 7 is a perspective illustration of part of an apparatus configured to heat smokable material, in which the regions of smokable material are provided between pairs of upstanding heating plates.
Figure 8:
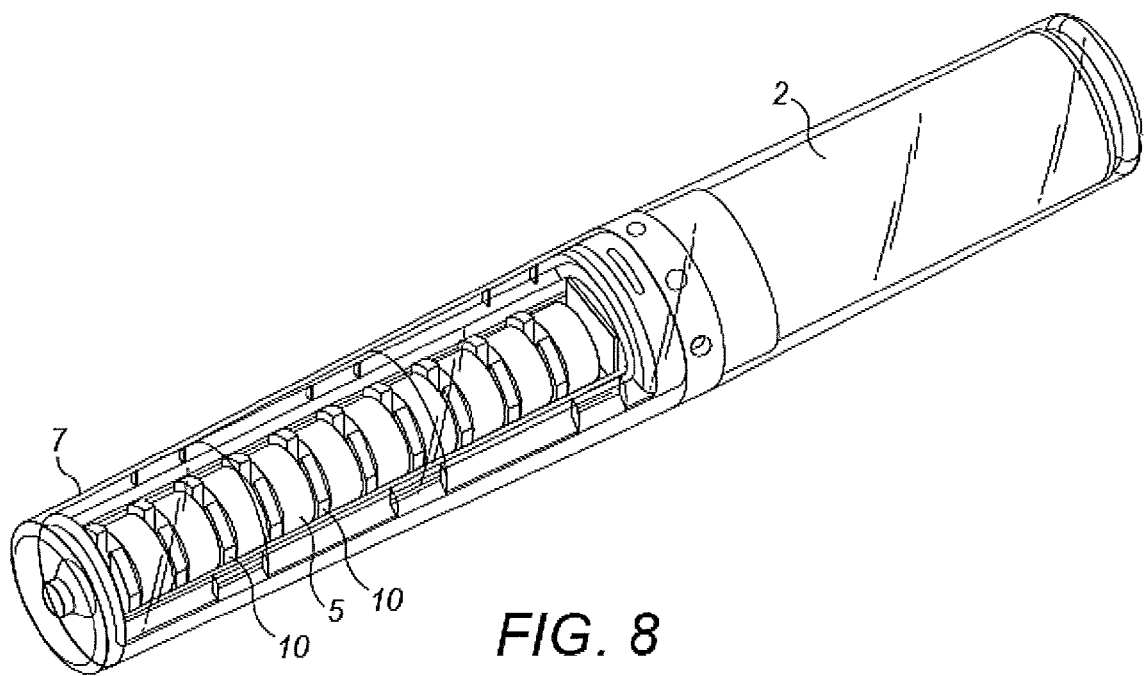
FIG. 8 is a perspective illustration of the apparatus shown in FIG. 7, in which an external housing is additionally illustrated.

Alternatively, referring to FIGS. 7, 8 and 9, a different geometrical configuration of heater 3 and smokable material 5 can be used. More particularly, the heater 3 can comprise a plurality of heating regions 10 which extend directly into an elongate heating chamber 4 which is divided into sections by the heating regions 10. During use, the heating regions 10 extend directly into an elongate smokable material cartridge 11 or other substantially solid body of smokable material 5. The smokable material 5 in the heating chamber 4 is thereby divided into discrete sections separated from each other by the spaced-apart heating regions 10. The heater 3, heating chamber 4 and smokable material 5 may extend together along a central, longitudinal axis of the housing 7. As shown in FIGS. 7 and 9, the heating regions 10 may each comprise a projection 10, such as an upstanding heating plate 10, which extends into the body of smokable material 5. The projections 10 are discussed below in the context of heating plates 10. The principal plane of the heating plates 10 may be substantially perpendicular to the principal longitudinal axis of the body of smokable material 5 and heating chamber 4 and/or housing 7. The heating plates 10 may be parallel to one another, as shown in FIGS. 7 and 9. Each section of smokable material 5 is bounded by a main heating surface of a pair of heating plates 10 located either side of the smokable material section, so that activation of one or both of the heating plates 10 will cause thermal energy to be transferred directly into the smokable material 5. The heating surfaces may be embossed to increase the surface area of the heating plate 10 against the smokable material 5. Optionally, each heating plate 10 may comprise a thermally reflective layer which divides the plate 10 into two halves along its principal plane. Each half of the plate 10 can thus constitute a separate heating region 10 and may be independently activated to heat only the section of smokable material 5 which lies directly against that half of the plate 10, rather than the smokable material 5 on both sides of the plate 10. Adjacent plates 10, or facing portions thereof, may be activated to heat a section of smokable material 5, which is located between the adjacent plates, from substantially opposite sides of the section of smokable material 5.

The elongate smokable material cartridge or body 11 can be installed between, and removed from, the heating chamber 4 and heating plates 10 by removing a section of the housing 7 at the housing's second end 9, as previously described. The heating regions 10 can be individually and selectively activated to heat different sections of the smokable material 5 as required.

In this way, when a particular one or pair of the heating regions 10 is activated, it supplies thermal energy to the smokable material 5 located directly adjacent to the heating region(s) 10 without substantially heating the remainder of the smokable material 5. The heated section of smokable material 5 may comprise a radial section of smokable material 5 located between the heating regions 10, as shown in FIGS. 7 to 9.

The apparatus 1 may comprise a controller 12, such as a microcontroller 12, which is configured to control operation of the apparatus 1. The controller 12 is electronically connected to the other components of the apparatus 1 such as the energy source 2 and heater 3 so that it can control their operation by sending and receiving signals. The controller 12 is, in particular, configured to control activation of the heater 3 to heat the smokable material 5. For example, the controller 12 may be configured to activate the heater 3, which may comprise selectively activating one or more heating regions 10, in response to a user drawing on the mouthpiece 6 of the apparatus 1. In this regard, the controller 12 may be in communication with a puff sensor 13 via a suitable communicative coupling. The puff sensor 13 is configured to detect when a puff occurs at the mouthpiece 6 and, in response, is configured to send a signal to the controller 12 indicative of the puff. An electronic signal may be used. The controller 12 may respond to the signal from the puff sensor 13 by activating the heater 3 and thereby heating the smokable material 5. The use of a puff sensor 13 to activate the heater 3 is not, however, essential and other means for providing a stimulus to activate the heater 3 can alternatively be used. For example, the controller 12 may activate the heater 3 in response to another type of activation stimulus such as actuation of a user-operable actuator. The volatilized compounds released during heating can then be inhaled by the user through the mouthpiece 6. The controller 12 can be located at any suitable position within the housing 7. An example position is between the energy source 2 and the heater 3/heating chamber 4, as illustrated in FIG. 3.

If the heater 3 comprises two or more heating regions 10 as described above, the controller 12 may be configured to activate the heating regions 10 in a predetermined order or pattern. For example, the controller 12 may be configured to activate the heating regions 10 sequentially along or around the heating chamber 4. Each activation of a heating region 10 may be in response to detection of a puff by the puff sensor 13 or may be triggered in an alternative way, as described further below.

Figure 10:
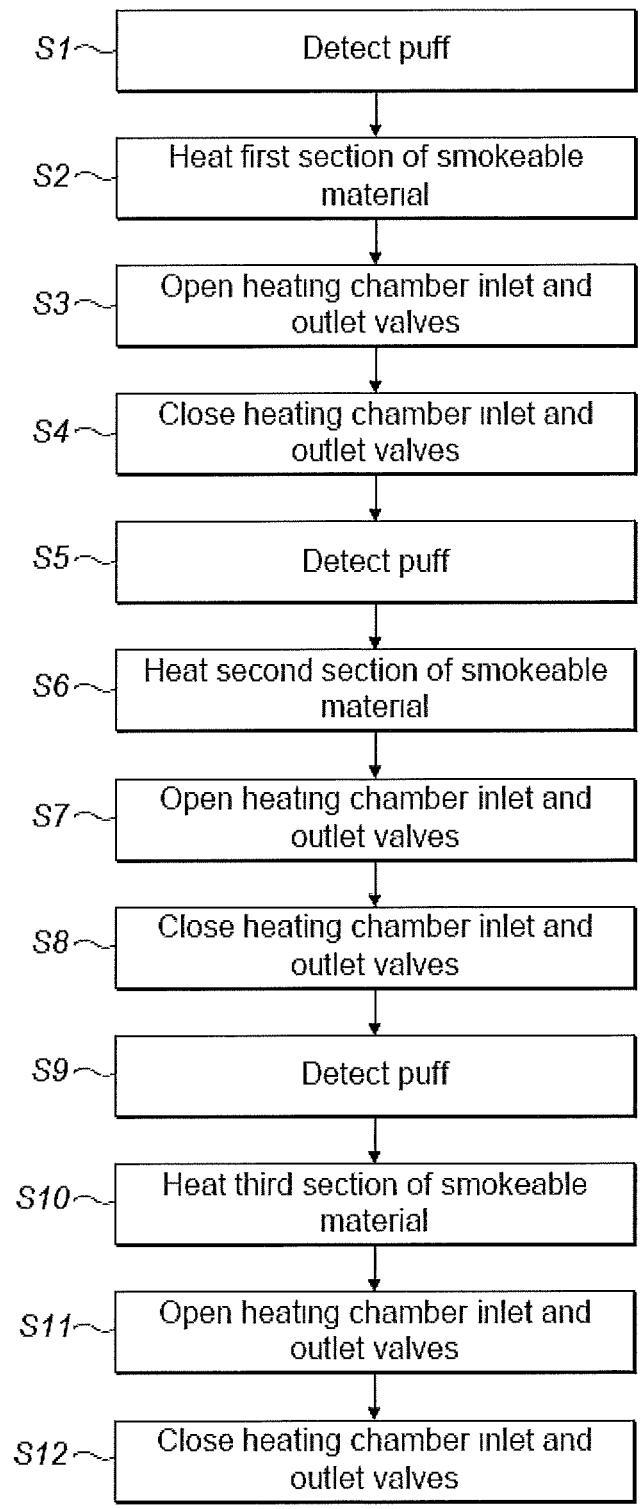
FIG. 10 is a flow diagram showing a method of activating heating regions and opening and closing heating chamber valves during puffing.

Referring to FIG. 10, an example heating method may comprise a first step S1 in which an activation stimulus such as a first puff is detected followed by a second step S2 in which a first section of smokable material 5 is heated in response to the first puff or other activation stimulus. In a third step S3, hermetically sealable inlet and outlet valves 24 may be opened to allow air to be drawn through the heating chamber 4 and out of the apparatus 1 through the mouthpiece 6. In a fourth step, the valves 24 are closed. These valves 24 are described in more detail below with respect to FIG. 20. In fifth S5, sixth S6, seventh S7 and eighth S8 steps, a second section of smokable material 5 may be heated in response to a second activation stimulus such as a second puff, with a corresponding opening and closing of the heating chamber inlet and outlet valves 24. In ninth S9, tenth S10, eleventh S11 and twelfth S12 steps, a third section of the smokable material 5 may be heated in response to a third activation stimulus such as a third puff with a corresponding opening and closing of the heating chamber inlet and outlet valves 24, and so on. As referred to above, means other than a puff sensor 13 could alternatively be used. For example, a user of the apparatus 1 may actuate a control switch to indicate that he/she is taking a new puff. In this way, a fresh section of smokable material 5 may be heated to volatilize nicotine and aromatic compounds for each new puff. The number of heating regions 10 and/or independently heatable sections of smokable material 5 may correspond to the number of puffs for which the cartridge 11 is intended to be used. Alternatively, each independently heatable smokable material section 5 may be heated by its corresponding heating region(s) 10 for a plurality of puffs such as two, three or four puffs, so that a fresh section of smokable material 5 is heated only after a plurality of puffs have been taken whilst heating the previous smokable material section.

Instead of activating each heating region 10 in response to an individual puff, the heating regions 10 may alternatively be activated sequentially, one after the other, in response to a single, initial puff at the mouthpiece 6. For example, the heating regions 10 may be activated at regular, predetermined intervals over the expected inhalation period for a particular smokable material cartridge 11. The inhalation period may, for example, be between approximately one and approximately four minutes. Therefore, at least the fifth and ninth steps S5, S9 shown in FIG. 10 are optional. Each heating region 10 may be activated for a predetermined period corresponding to the duration of the single or plurality of puffs for which the corresponding independently heatable smokable material section 5 is intended to be heated. Once all of the heating regions 10 have been activated for a particular cartridge 11, the controller 12 may be configured to indicate to the user that the cartridge 11 should be changed. The controller 12 may, for example, activate an indicator light at the external surface of the housing 7.

It will be appreciated that activating individual heating regions 10 in order rather than activating the entire heater 3 means that the energy required to heat the smokable material 5 is reduced over what would be required if the heater 3 were activated fully over the entire inhalation period of a cartridge 11. Therefore, the maximum required power output of the energy source 2 is also reduced. This means that a smaller and lighter energy source 2 can be installed in the apparatus 1.

Figure 12:
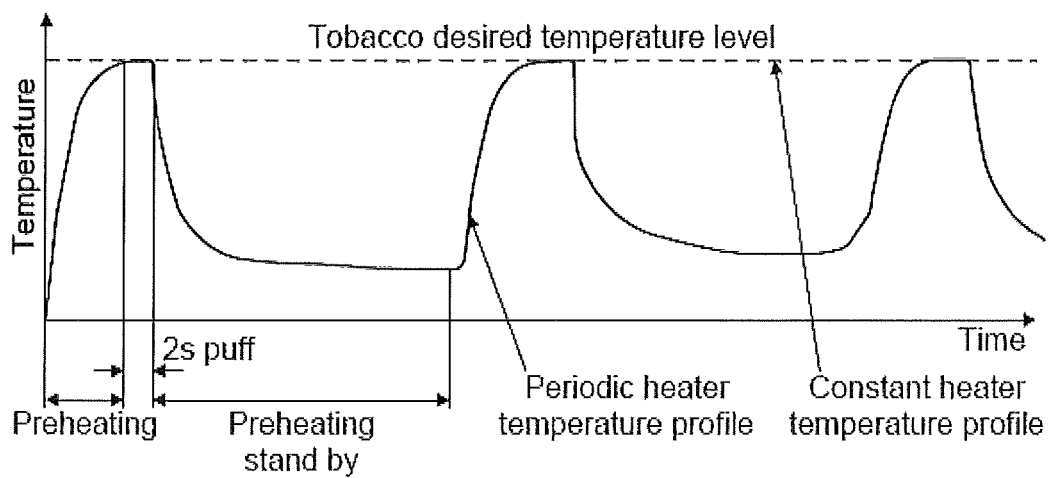
FIG. 12 is a graphical illustration of a heating pattern which can be used to heat smokable material using a heater.

The controller 12 may be configured to de-activate the heater 3, or reduce the power being supplied to the heater 3, in between puffs. This saves energy and extends the life of the energy source 2. For example, upon the apparatus 1 being switched on by a user or in response to some other stimulus, such as detection of a user placing their mouth against the mouthpiece 6, the controller 12 may be configured to cause the heater 3, or next heating region 10 to be used to heat the smokable material 5, to be partially activated so that it heats up in preparation to volatilize components of the smokable material 5. The partial activation does not heat the smokable material 5 to a sufficient temperature to volatilize nicotine. A suitable temperature could be below 120° C., such as 100° C. or below. An example is a temperature between 60° C. and 100° C., such as a temperature between 80° C. and 100° C. The temperature may be less than 100° C. In response to detection of a puff by the puff sensor 13, the controller 12 can then cause the heater 3 or heating region 10 in question to heat the smokable material 5 further in order to rapidly volatilize the nicotine and other aromatic compounds for inhalation by the user. If the smokable material 5 comprises tobacco, a suitable temperature for volatilizing the nicotine and other aromatic compounds may be 100° C. or above, such as 120° C. or above. An example is a temperature between 100° C. and 250° C., such as between 100° C. and 220° C., between 100° C. and 200° C., between 150° C. and 250° C. or between 130° C. and 180° C. The temperature may be more than 100° C. An example full activation temperature is 150° C., although other values such as 250° C. are also possible. A super-capacitor can optionally be used to provide the peak current used to heat the smokable material 5 to the volatization temperature. An example of a suitable heating pattern is shown in FIG. 12, in which the peaks may respectively represent the full activation of different heating regions 10. As can be seen, the smokable material 5 is maintained at the volatization temperature for the approximate period of the puff which, in this example, is two seconds.

Three example operational modes of the heater 3 are described below.

In a first operational mode, during full activation of a particular heating region 10, all other heating regions 10 of the heater are deactivated. Therefore, when a new heating region 10 is activated, the previous heating region is deactivated. Power is supplied only to the activated region 10.

Alternatively, in a second operational mode, during full activation of a particular heating region 10, one or more of the other heating regions 10 may be partially activated. Partial activation of the one or more other heating regions 10 may comprise heating the other heating region(s) 10 to a temperature which is sufficient to substantially prevent condensation of components such as nicotine volatized from the smokable material 5 in the heating chamber 4. The temperature of the heating regions 10 which are partially activated is less than the temperature of the heating region 10 which is fully activated. The smokable material 10 located adjacent the partially activated regions 10 is not heated to a temperature sufficient to volatize components of the smokable material 5.

Alternatively, in a third operational mode, once a particular heating region 10 has been activated, it remains fully activated until the heater 3 is switched off. Therefore, the power supplied to the heater 3 incrementally increases as more of the heating regions 10 are activated during inhalation from the cartridge 11. As with the second mode previously described, the continuing activation of the heating regions 10 substantially prevent condensation of components such as nicotine volatized from the smokable material 5 in the heating chamber 4.

Figure 19:
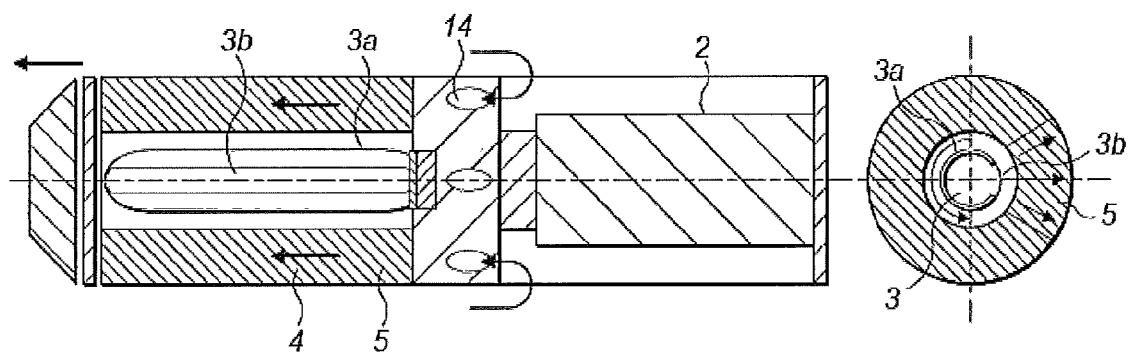
FIG. 19 is a schematic, cross-sectional illustration of a heat shield and a heat-transparent window which are moveable relative to a body of smokable material to selectively allow thermal energy to be transmitted to different sections of the smokable material through the window.

The apparatus 1 may comprise a heat shield 3a, which is located between the heater 3 and the heating chamber 4/smokable material 5. The heat shield 3a is configured to substantially prevent thermal energy from flowing through the heat shield 3a and therefore can be used to selectively prevent the smokable material 5 from being heated even when the heater 3 is activated and emitting thermal energy. Referring to FIG. 19, the heat shield 3a may, for example, comprise a cylindrical layer of heat reflective material which is located co-axially around the heater 3. Alternatively, if the heater 3 is located around the heating chamber 4 and smokable material 5 as previously described, the heat shield 3a may comprise a cylindrical layer of heat reflective material which is located co-axially around the heating chamber 4 and co-axially inside of the heater 3. The heat shield 3a may additionally or alternatively comprise a heat-insulating layer configured to insulate the heater 3 from the smokable material 5. The heat shield 3a comprises a substantially heat-transparent window 3b which allows thermal energy to propagate through the window 3b and into the heating chamber 4 and smokable material 5. Therefore, the section of smokable material 5 which is aligned with the window 3b is heated whilst the remainder of the smokable material 5 is not. The heat shield 3a and window 3b may be rotatable or otherwise moveable with respect to the smokable material 5 so that different sections of the smokable material 5 can be selectively and individually heated by rotating or moving the heat shield 3a and window 3b. The effect is similar to the effect provided by selectively and individually activating the heating regions 10 referred to above. For example, the heat shield 3a and window 3b may be rotated or otherwise moved incrementally in response to a signal from the puff detector 13. Additionally or alternatively, the heat shield 3a and window 3b may be rotated or otherwise moved incrementally in response to a predetermined heating period having elapsed. Movement or rotation of the heat shield 3a and window 3b may be controlled by electronic signals from the controller 12. The relative rotation or other movement of the heat shield 3a/window 3b and smokable material 5 may be driven by a stepper motor 3c under the control of the controller 12. This is illustrated in FIG. 19. Alternatively, the heat shield 3a and window 3b may be manually rotated using a user control such as an actuator on the housing 7. The heat shield 3a does not need to be cylindrical and may comprise optionally comprise one or more suitably positioned longitudinally extending elements and or/plates.

It will be appreciated that a similar result can be obtained by rotating or moving the smokable material 5 relative to the heater 3, heat shield 3a and window 3b. For example, the heating chamber 4 may be rotatable around the heater 3. If this is the case, the above description relating to movement of the heat shield 3a can be applied instead to movement of the heating chamber 4 relative to the heat shield 3a.

The heat shield 3a may comprise a coating on the longitudinal surface of the heater 3. In this case, an area of the heater's surface is left uncoated to form the heat-transparent window 3b. The heater 3 can be rotated or otherwise moved, for example under the control of the controller 12 or user controls, to cause different sections of the smokable material 5 to be heated. Alternatively, the heat shield 3a and window 3b may comprise a separate shield 3a which is rotatable or otherwise moveable relative to both the heater 3 and the smokable material 5 under the control of the controller 12 or other user controls.

Figure 11:
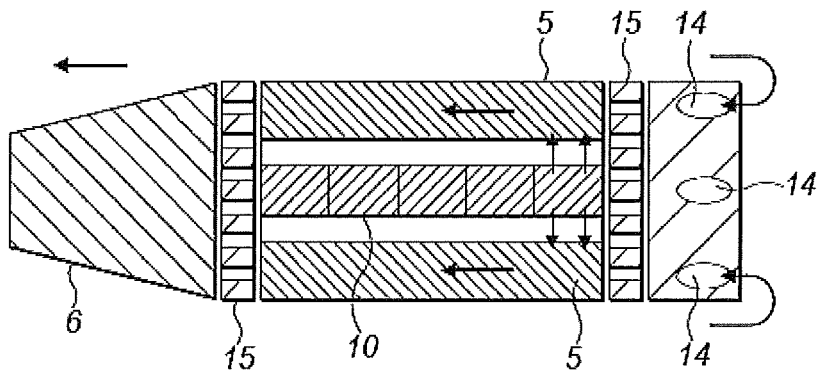
FIG. 11 is a schematic illustration of a gaseous flow through an apparatus configured to heat smokable material.

Referring to FIG. 6, the apparatus 1 may comprise air inlets 14 which allow external air to be drawn into the housing 7 and through the heated smokable material 5 during puffing. The air inlets 14 may comprise apertures 14 in the housing 7 and may be located upstream from the smokable material 5 and heating chamber 4 towards the first end 8 of the housing 7. This is shown in FIG. 1. Another example is shown in FIG. 11. Air drawn in through the inlets 14 travels through the heated smokable material 5 and therein is enriched with smokable material vapours, such as aroma vapours, before being inhaled by the user at the mouthpiece 6. Optionally, as shown in FIG. 11, the apparatus 1 may comprise a heat exchanger 15 configured to warm the air before it enters the smokable material 5 and/or to cool the air before it is drawn through the mouthpiece 6. For example, the heat exchanger 15 may be configured to use heat extracted from the air entering the mouthpiece 6 to warm new air before it enters the smokable material 5.

The apparatus 1 may comprise a smokable material compressor 16 configured to cause the smokable material 5 to compress upon activation of the compressor 16. The apparatus 1 can also comprise a smokable material expander 17 configured to cause the smokable material 5 to expand upon activation of the expander 17. The compressor 16 and expander 17 may, in practice, be implemented as the same unit as will be explained below. The smokable material compressor 16 and expander 17 may optionally operate under the control of the controller 12. In this case, the controller 12 is configured to send a signal, such as an electrical signal, to the compressor 16 or expander 17 which causes the compressor 16 or expander 17 to respectively compress or expand the smokable material 5. Alternatively, the compressor 16 and expander 17 may be actuated by a user of the apparatus 1 using a manual control on the housing 7 to compress or expand the smokable material 5 as required.

The compressor 16 is principally configured to compress the smokable material 5 and thereby increase its density during heating. Compression of the smokable material increases the thermal conductivity of the body of smokable material 5 and therefore provides a more rapid heating and consequent rapid volatization of nicotine and other aromatic compounds. This is preferable because it allows the nicotine and aromatics to be inhaled by the user without substantial delay in response to detection of a puff. Therefore, the controller 12 may activate the compressor 16 to compress the smokable material 5 for a predetermined heating period, for example one second, in response to detection of a puff. The compressor 16 may be configured to reduce its compression of the smokable material 5, for example under the control of the controller 12, after the predetermined heating period. Alternatively, the compression may be reduced or automatically ended in response to the smokable material 5 reaching a predetermined threshold temperature. A suitable threshold temperature may be in the range of approximately 100° C. to 250° C., such as between 100° C. and 220° C., between 150° C. and 250° C., between 100° C. and 200° C. or between 130° C. and 180° C. The threshold temperature may be above 100° C., such as a value above 120° C., and may be user selectable. A temperature sensor may be used to detect the temperature of the smokable material 5.

The expander 17 is principally configured to expand the smokable material 5 and thereby decrease its density during puffing. The arrangement of smokable material 5 in the heating chamber 4 becomes more loose when the smokable material 5 has been expanded and this aids the gaseous flow, for example air from the inlets 14, through the smokable material 5. The air is therefore more able to carry the volatilized nicotine and aromatics to the mouthpiece 6 for inhalation. The controller 12 may activate the expander 17 to expand the smokable material 5 immediately following the compression period referred to above so that air can be drawn more freely through the smokable material 5. Actuation of the expander 17 may be accompanied by a user-audible sound or other indication to indicate to the user that the smokable material 5 has been heated and that puffing can commence.

Figure 13:
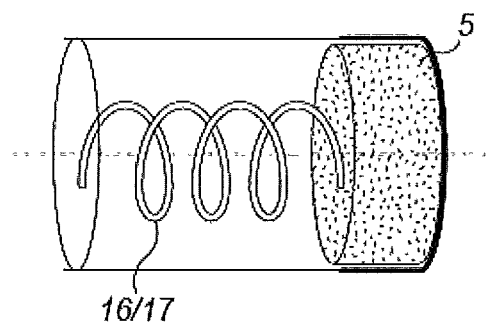
FIG. 13 is a schematic illustration of a smokable material compressor configured to compress smokable material during heating.
Figure 14:
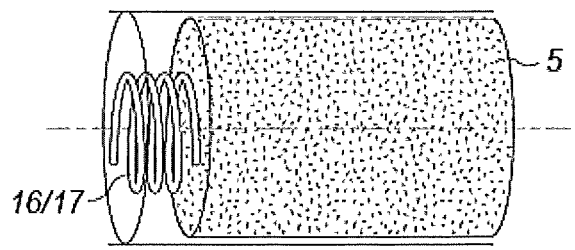
FIG. 14 is a schematic illustration of a smokable material expander configured to expand smokable material during puffing.
Figure 15:
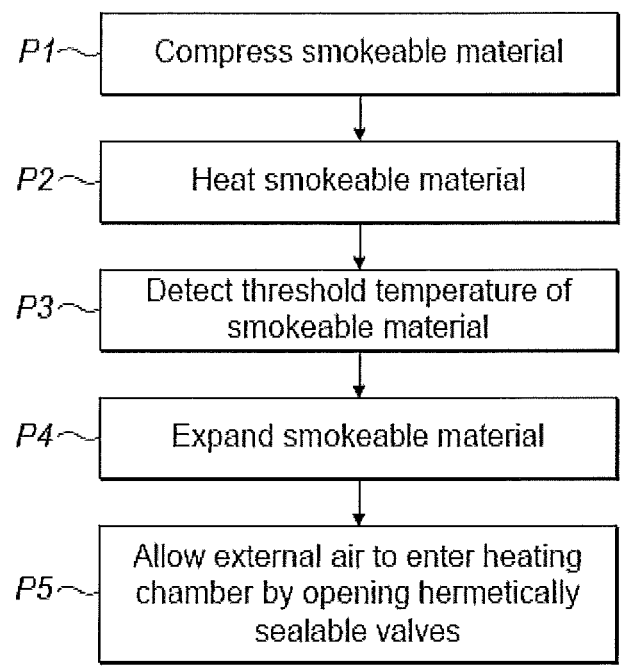
FIG. 15 is a flow diagram showing a method of compressing smokable material during heating and expanding the smokable material for puffing.

Referring to FIGS. 13 and 14, the compressor 16 and expander 17 may comprise a spring-actuated driving rod which is configured to compress the smokable material 5 in the heating chamber 4 when the spring is released from compression. This is schematically illustrated in FIGS. 13 and 14, although it will be appreciated that other implementations could be used. For example, the compressor 16 may comprise a ring, having a thickness approximately equal to the tubular-shaped heating chamber 4 described above, which is driven by a spring or other means into the heating chamber 4 to compress the smokable material 5. Alternatively, the compressor 16 may be comprised as part of the heater 3 so that the heater 3 itself is configured to compress and expand the smokable material 5 under the control of the controller 12. For example, where the heater 3 comprises upstanding heating plates 10 of the type previously described, the plates 10 may be independently moveable in a longitudinal direction of the heater 3 to expand or compress the sections of smokable material 5 which are located adjacent to them. A method of compressing and expanding the smokable material 5 is shown in FIG. 15.

Thermal insulation 18 may be provided between the smokable material 5 and an external surface 19 of the housing 7 to reduce heat loss from the apparatus 1 and therefore improve the efficiency with which the smokable material 5 is heated. For example, referring to FIG. 1, a wall of the housing 7 may comprise a layer of insulation 18 which extends around the outside of the heating chamber 4. The insulation layer 18 may comprise a substantially tubular length of insulation 18 located co-axially around the heating chamber 4 and smokable material 5. This is shown in FIG. 1. Another example is shown in FIG. 21. It will be appreciated that the insulation 18 could also be comprised as part of the smokable material cartridge 11, in which it would be located co-axially around the outside of the smokable material 5.

Figure 16:
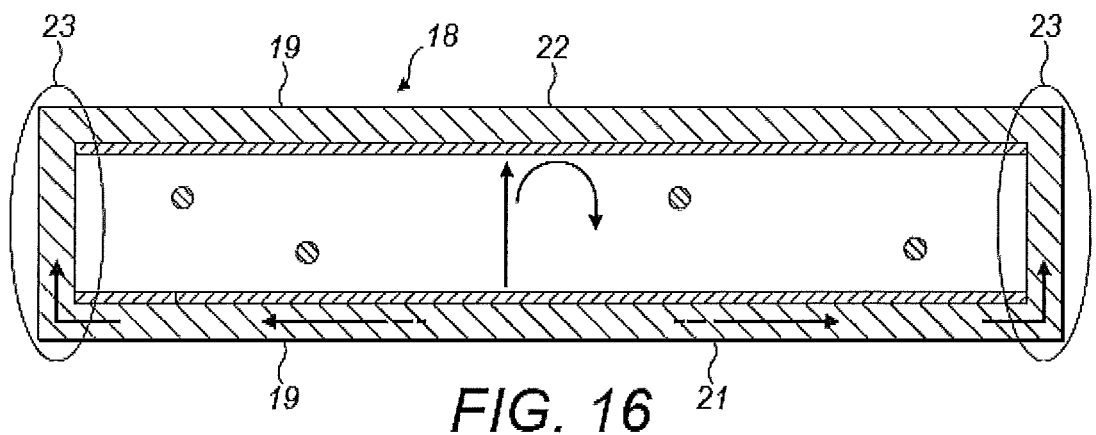
FIG. 16 is a schematic, cross-sectional illustration of a section of vacuum insulation configured to insulate heated smokable material from heat loss.

Referring to FIG. 16, the insulation 18 may comprise vacuum insulation 18. For example, the insulation 18 may comprise a layer which is bounded by a wall material 19 such as a metallic material. An internal region or core 20 of the insulation 18 may comprise an open-cell porous material, for example comprising polymers, aerogels or other suitable material, which is evacuated to a low pressure. The pressure in the internal region 20 may be in the range of 0.1 to 0.001 mbar. The wall 19 of the insulation 18 is sufficiently strong to withstand the force exerted against it due to the pressure differential between the core 20 and external surfaces of the wall 19, thereby preventing the insulation 18 from collapsing. The wall 19 may, for example, comprise a stainless steel wall 19 having a thickness of approximately 100 µm. The thermal conductivity of the insulation 18 may be in the range of 0.004 to 0.005 W/mK. The heat transfer coefficient of the insulation 18 may be between approximately 1.10 $W/(m^2K)$ and approximately 1.40 $W/(m^2K)$ within a temperature range of between 100° C. and 250° C., such as between approximately 150 degrees Celsius and approximately 250 degrees Celsius. The gaseous conductivity of the insulation 18 is negligible. A reflective coating may be applied to the internal surfaces of the wall material 19 to minimize heat losses due to radiation propagating through the insulation 18. The coating may, for example, comprise an aluminium IR reflective coating having a thickness of between approximately 0.3 µm and 1.0 µm. The evacuated state of the internal core region 20 means that the insulation 18 functions even when the thickness of the core region 20 is very small. The insulating properties are substantially unaffected by its thickness. This helps to reduce the overall size of the apparatus 1.

As shown in FIG. 16, the wall 19 may comprise an inwardly-facing section 21 and an outwardly-facing section 22. The inwardly-facing section 21 substantially faces the smokable material 5 and heating chamber 4. The outwardly-facing section 22 substantially faces the exterior of the housing 7. During operation of the apparatus 1, the inwardly-facing section 21 may be warmer due to the thermal energy originating from the heater 3, whilst the outwardly-facing section 22 is cooler due to the effect of the insulation 18. The inwardly-facing section 21 and the outwardly-facing section 22 may, for example, comprise substantially parallel longitudinally-extending walls 19 which are at least as long as the heater 3. The internal surface of the outwardly-facing wall section 22, i.e. the surface facing the evacuated core region 20, may comprise a coating for absorbing gas in the core 20. A suitable coating is a titanium oxide film.

The thermal insulation 18 may comprise hyper-deep vacuum insulation such as an Insulon® Shaped-Vacuum Thermal Barrier as described in U.S. Pat. No. 7,374,063. The overall thickness of such insulation 18 may be extremely small. An example thickness is between approximately 1 mm and approximately 1 µm, such as approximately 0.1 mm, although other larger or smaller thicknesses are also possible. The thermally insulating properties of the insulation 18 are substantially unaffected by its thickness and therefore thin insulation 18 can be used without any substantial additional heat loss from the apparatus 1. The very small thickness of the thermal insulation 18 may allow the size of the housing 7 and apparatus 1 as a whole to be reduced beyond the sizes previously discussed and may allow the thickness, for example the diameter, of the apparatus 1 to be approximately equal to smoking articles such as cigarettes, cigars and cigarillos. The weight of the apparatus 1 may also be reduced, providing similar benefits to the size reductions discussed above.

Although the thermal insulation 18 described previously may comprise a gas-absorbing material to maintain or aid with creation of the vacuum in the core region 20, a gas absorbing material is not used in the deep-vacuum insulation 18. The absence of the gas absorbing material aids with keeping the thickness of the insulation 18 very low and thus helps to reduce the overall size of the apparatus 1.

Figure 22:
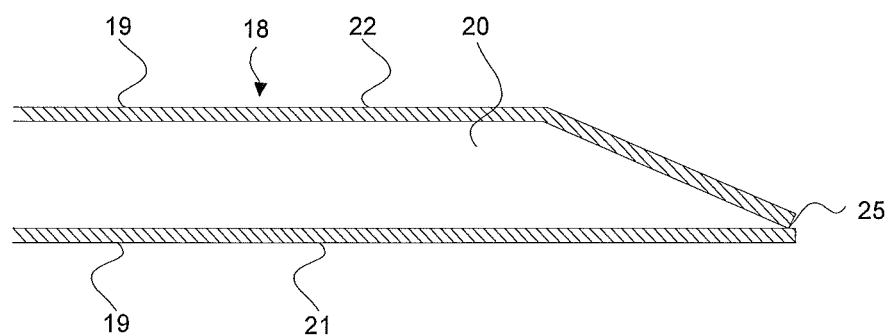
FIG. 22 is a schematic, cross sectional illustration of a partial section of deep-vacuum insulation configured to thermally insulate an apparatus configured to heat smokable material.

The geometry of the hyper-deep insulation 18 allows the vacuum in the insulation to be deeper than the vacuum used to extract molecules from the core region 20 of the insulation 18 during manufacture. For example, the deep vacuum inside the insulation 18 may be deeper than that of the vacuum-furnace chamber in which it is created. The vacuum inside the insulation 18 may, for example, be of the order $10^{-7}$ Torr. Referring to FIG. 22, an end of the core region 20 of the deep-vacuum insulation 18 may taper as the outwardly facing section 22 and inwardly facing section 21 converge to an outlet 25 through which gas in the core region 20 may be evacuated to create a deep vacuum during manufacture of the insulation 18. FIG. 22 illustrates the outwardly facing section 22 converging towards the inwardly facing section 21 but a converse arrangement, in which the inwardly facing section 21 converges to the outwardly facing section 22, could alternatively be used. The converging end of the insulating wall 19 is configured to guide gas molecules in the core region 20 out of the outlet 25 and thereby create a deep vacuum in the core 20. The outlet 25 is sealable so as to maintain a deep vacuum in the core region 20 after the region 20 has been evacuated. The outlet 25 can be sealed, for example, by creating a brazed seal at the outlet 25 by heating brazing material at the outlet 25 after gas has been evacuated from the core 20. Alternative sealing techniques could be used.

In order to evacuate the core region 20, the insulation 18 may be placed in a low pressure, substantially evacuated environment such as a vacuum furnace chamber so that gas molecules in the core region 20 flow into the low pressure environment outside the insulation 18. When the pressure inside the core region 20 becomes low, the tapered geometry of the core region 20, and in particular the converging sections 21, 22 referred to above, becomes influential in guiding remaining gas molecules out the core 20 via the outlet 25. Specifically, when the gas pressure in the core region 20 is low, the guiding effect of the converging inwardly and outwardly facing sections 21, 22 is effective to channel the remaining gas molecules inside the core 20 towards the outlet 25 and make the probability of gas exiting the core 20 higher than the probability of gas entering the core 20 from the external, low pressure environment. In this way, the geometry of the core 20 allows the pressure inside the core 20 to be reduced below the pressure of the environment outside the insulation 18.

Optionally, as previously described, one or more low emissivity coatings may be present on the internal surfaces of the inwardly and outwardly facing sections 21, 22 of the wall 19 in order to substantially prevent heat losses by radiation.

Although the shape of the insulation 18 is generally described herein as substantially cylindrical or similar, the thermal insulation 18 could be another shape, for example in order to accommodate and insulate a different configuration of the apparatus 1 such as different shapes and sizes of heating chamber 4, heater 3, housing 7 or energy source 2. For example, the size and shape of deep-vacuum insulation 18 such as an Insulon® Shaped-Vacuum Thermal Barrier referred to above is substantially unlimited by its manufacturing process. Suitable materials for forming the converging structure described above include ceramics, metals, metalloids and combinations of these.

Figure 17:
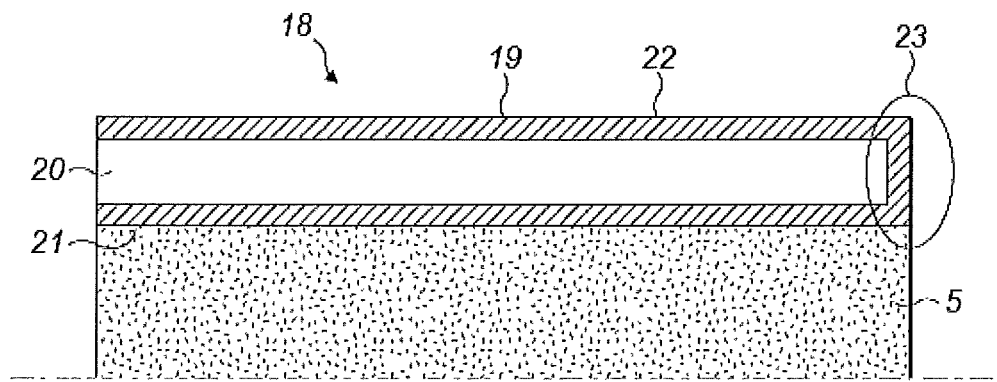
FIG. 17 is another schematic, cross-sectional illustration of a section of vacuum insulation configured to insulate heated smokable material from heat loss.

Referring to the schematic illustration in FIG. 17, a thermal bridge 23 may connect the inwardly-facing wall section 21 to the outwardly-facing wall section 22 at one or more edges of the insulation 18 in order to completely encompass and contain the low pressure core 20. The thermal bridge 23 may comprise a wall 19 formed of the same material as the inwardly and outwardly-facing sections 21, 22. A suitable material is stainless steel, as previously discussed. The thermal bridge 23 has a greater thermal conductivity than the insulating core 20 and therefore may undesirably conduct heat out of the apparatus 1 and, in doing so, reduce the efficiency with which the smokable material 5 is heated.

Figure 18:
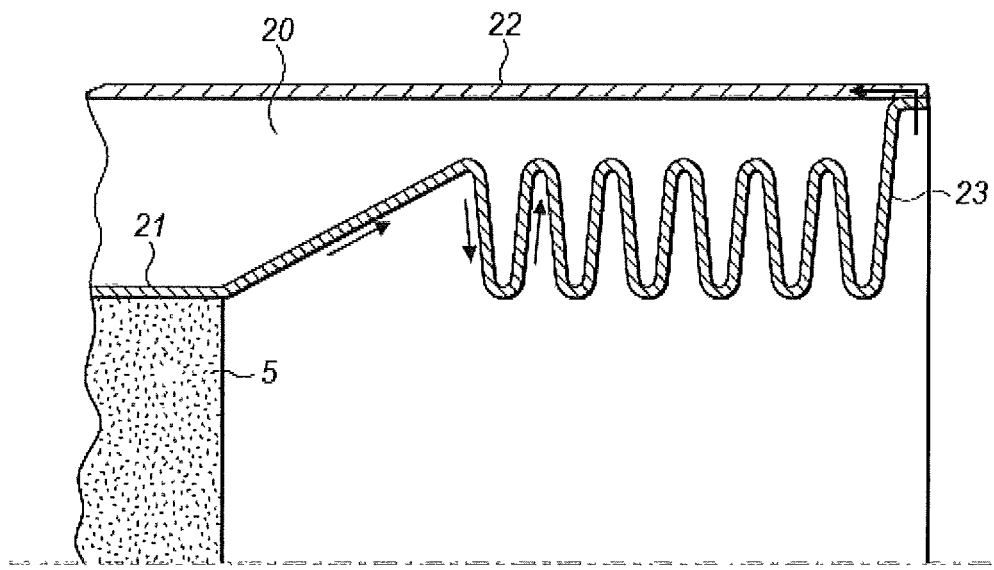
FIG. 18 is a schematic, cross-sectional illustration of a heat resistive thermal bridge which follows an indirect path from a higher temperature insulation wall to a lower temperature insulation wall.

To reduce heat losses due to the thermal bridge 23, the thermal bridge 23 may be extended to increase its resistance to heat flow from the inwardly-facing section 21 to the outwardly-facing section 22. This is schematically illustrated in FIG. 18. For example, the thermal bridge 23 may follow an indirect path between the inwardly-facing section 21 of wall 19 and the outwardly-facing section 22 of wall 19. This may be facilitated by providing the insulation 18 over a longitudinal distance which is longer than the lengths of the heater 3, heating chamber 4 and smokable material 5 so that the thermal bridge 23 can gradually extend from the inwardly-facing section 21 to the outwardly-facing section 22 along the indirect path, thereby reducing the thickness of the core 20 to zero, at a longitudinal location in the housing 7 where the heater 3, heating chamber 4 and smokable material 5 are not present.

Figure 20:
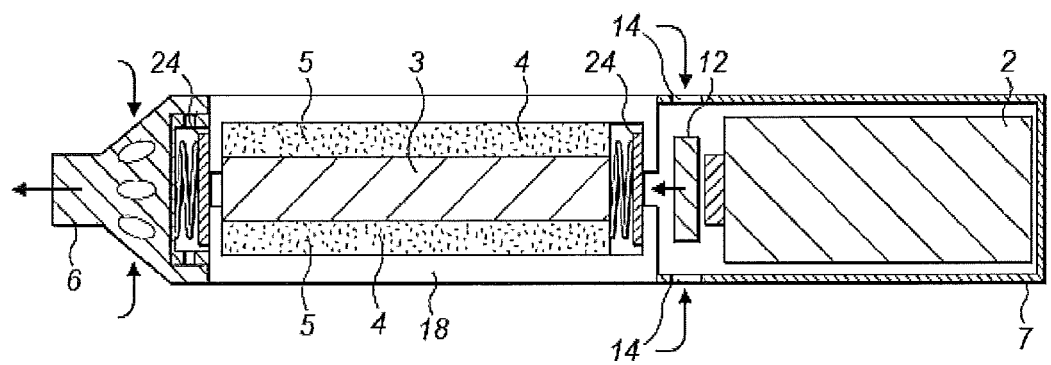
FIG. 20 is schematic, cross sectional illustration of part of an apparatus configured to heat smokable material, in which a heating chamber is hermetically sealable by check valves.

Referring to FIG. 20, as previously discussed, the heating chamber 4 insulated by the insulation 18 may comprise inlet and outlet valves 24 which hermetically seal the heating chamber 4 when closed. The valves 24 can thereby prevent air from undesirably entering and exiting the chamber 4 and can prevent smokable material flavours from exiting the chamber 4. The inlet and outlet values 24 may, for example, be provided in the insulation 18. For example, between puffs, the valves 24 may be closed by the controller 12 so that all volatilized substances remain contained inside the chamber 4 in-between puffs. The partial pressure of the volatized substances between puffs reaches the saturated vapour pressure and the amount of evaporated substances therefore depends only on the temperature in the heating chamber 4. This helps to ensure that the delivery of volatilized nicotine and aromatic compounds remains constant from puff to puff. During puffing, the controller 12 is configured to open the valves 24 so that air can flow through the chamber 4 to carry volatilized smokable material components to the mouthpiece 6. A membrane can be located in the valves 24 to ensure that no oxygen enters the chamber 4. The valves 24 may be breath-actuated so that the valves 24 open in response to detection of a puff at the mouthpiece 6. The valves 24 may close in response to a detection that a puff has ended. Alternatively, the valves 24 may close following the elapse of a predetermined period after their opening. The predetermined period may be timed by the controller 12. Optionally, a mechanical or other suitable opening/closing means may be present so that the valves 24 open and close automatically. For example, the gaseous movement caused by a user puffing on the mouthpiece 6 may be used to open and close the valves 24. Therefore, the use of the controller 12 is not necessarily required to actuate the valves 24.

The mass of the smokable material 5 which is heated by the heater 3, for example by each heating region 10, may be in the range of 0.2 to 1.0 g. The temperature to which the smokable material 5 is heated may be user controllable, for example to any temperature within the temperature range of 100° C. to 250° C., such as any temperature within the range of 150° C. to 250° C. and the other volatizing temperature ranges previously described. The mass of the apparatus 1 as a whole may be in the range of 70 to 125 g. A battery 2 with a capacity of 1000 to 3000 mAh and voltage of 3.7V can be used. The heating regions 10 may be configured to individually and selectively heat between approximately 10 and 40 sections of smokable material 5 for a single cartridge 11.

It will be appreciated that any of the alternatives described above can be used singly or in combination. For example, as discussed above, the heater 3 may be located around the outside of the smokable material 5 rather than the smokable material 5 being located around the heater 3. The heater 3 may therefore circumscribe the smokable material 5 to apply heat to the smokable material 5 in a substantially radially inward direction.

In order to address various issues and advance the art, the entirety of this disclosure shows by way of illustration various embodiments in which the claimed invention(s) may be practiced and provide for superior apparatus. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An apparatus configured to heat smokable material to volatilize at least one component of the smokable material, comprising:
    a housing;
    a smokable material heating chamber within the housing, the heating chamber being hollow tubular for removably receiving smokable material therein;
    a plurality of discrete heating rings within the housing, the heating rings being constructed and arranged to heat smokable material received in use in the smokable material heating chamber so as to volatilize at least one component of the smokable material; and
    a region of insulation having a core that is evacuated to a lower pressure than an exterior of the insulation, the region of insulation being located between the heating rings and the housing so as to reduce heat loss from the apparatus.

2. The apparatus according to claim 1, wherein the insulation is located co-axially around the heating chamber.

3. The apparatus according to claim 1, wherein the insulation comprises an exterior wall which encloses the core region, the wall comprising a layer of stainless steel having a thickness of at least approximately 100 microns.

4. The apparatus according to claim 1, wherein a thickness of the insulation is less than approximately 1 mm.

5. The apparatus according to claim 1, wherein a thickness of the insulation is less than approximately 0.1 mm.

6. The apparatus according to claim 1, wherein a thickness of the insulation is between approximately 1 mm and 0.001 mm.

7. The apparatus according to claim 1, wherein a pressure in the core region is between approximately 0.1 and approximately 0.001 mbar.

8. The apparatus according to claim 1, wherein a pressure in the core region is of the order $10^{-7}$ Torr.

9. The apparatus according to claim 1, wherein a wall of the region of insulation which defines the core region has a coating for absorbing gas in the core region.

10. The apparatus according to claim 9, wherein the coating for absorbing gas in the core region comprises titanium oxide.

11. The apparatus according to claim 1, wherein the apparatus is configured to heat the smokable material without combusting the smokable material.

* * * * *